(12) United States Patent
Miura

(10) Patent No.: US 6,372,231 B1
(45) Date of Patent: *Apr. 16, 2002

(54) GELATINOUS COMPOSITION

(75) Inventor: Yoshimasa Miura, Yokohama (JP)

(73) Assignee: Shiseido Company, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/390,627

(22) Filed: Sep. 7, 1999

(30) Foreign Application Priority Data

Sep. 8, 1998 (JP) ............................................. 10-272589

(51) Int. Cl.⁷ ............................. A61K 7/00; A61K 7/42; A61K 31/765; A61K 31/77; A61K 31/785
(52) U.S. Cl. ...................... 424/401; 424/59; 424/78.03; 424/400; 514/944
(58) Field of Search ................................. 424/400, 401, 424/78.03, 59; 514/944

(56) References Cited

U.S. PATENT DOCUMENTS 5,859,069 A * 1/1999 Yanagida .................. 514/772.3

FOREIGN PATENT DOCUMENTS

| EP | 0 407 089 A2 | 1/1991 |
| EP | 0 627 259 A2 | 12/1994 |
| JP | 62045656 | * 2/1987 |
| JP | 7-100358 | 4/1995 |
| WO | WO 94/28860 | 12/1994 |

OTHER PUBLICATIONS

Tomoyuki, Patent Abstracts of Japan, 62–054759, Oct. 03, 1987, Japan Patent Office, Japan. (Abstract).

* cited by examiner

Primary Examiner—Jose' G. Dees
Assistant Examiner—Marina Lamm
(74) Attorney, Agent, or Firm—Foley & Lardner

(57) ABSTRACT

A gelatinous composition comprising (i) at least one silicone oil, (ii) at least one specified polyether-modified silicone (iii) water, and (iv) at least one lower alcohol, which exhibit excellent stability with the elapse of time as well as good spreadability and good cosmetic persistency.

9 Claims, No Drawings

GELATINOUS COMPOSITION

BACKGROUND OF THE INVENTION

1. Field of the Invention

The present invention relates to a gelatinous composition, especially suitable for external use.

2. Description of the Related Art

Silicone oil is formulated in a wide variety of commercial products including make-up cosmetics, scalp and hair cosmetics from the characteristics thereof, such as the light spreadability and the refreshing feeling at the time of use. Silicone oil is especially used, with effecting the characteristics, in gelatinous products such as gelatinous foundations, sun screen gels, moisture gels, hair gels, antiperspirant gels.

As gelatinous compositions, a gelatinous composition containing 2–30 parts by weight of dextrin fatty acid esters in 100 parts by weight of silicone oil (JP-B-3-6179), gelatinous compositions containing organohydrogen polysiloxanes and low viscosity silicone oils (JP-A-63-152308), etc have been proposed.

However, these known gelatinous compositions containing silicone oil have problems of poor stability with the elapse of time and the separation of silicone oil.

Recently, although gelatinous cosmetic compositions containing silicone oil having excellent stability with the elapse of time have been proposed (see Japanese Patent Application No. 5-268168) (i.e., JP-A-7-100358), it is pointed out that some stickiness is felt and dewiness is insufficient at the time of use.

SUMMARY OF THE INVENTION

Accordingly, the object of the present invention is to provide a gelatinous composition containing silicone oil having an excellent stability with the elapse of time and having feelings of little stickiness and dewiness at the time of use.

The present inventors engaged in intensive research with the purpose of solving the above-mentioned problems and, as a result, found that the above-mentioned problems can be solved by formulating special silicone compounds and lower alcohols, whereby the present invention has been completed.

That is, in accordance with the present invention, there is provided a gelatinous composition comprising:

(i) at least one silicone oil, (ii) at least one polyether-modified silicone having the formula (I):

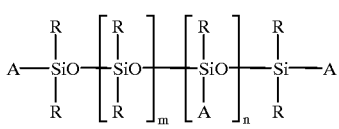

(I)

wherein A independently represents a group selected from the group consisting of a methyl group, phenyl group and polyoxyalkylene group having the formula (II):

(II)

wherein R' is a group selected from the group consisting of a hydrogen atom, an acyl group and alkyl groups having 1 to 4 carbon atoms, a and b are independently an integer of 0 to 50, provided that both a and b are not zero, R independently represents a methyl group or phenyl group, m is an integer of 1 to less than 50 and n is an integer of 1 to 40, provided that a part of the methyl group, phenyl group and polyoxyalkylene group may be substituted with a fluorine atom, and at least one polyoxyalkylene group is present in one molecule, (iii) water, and (iv) at least one lower alcohol.

In a gelatinous composition according to the present invention, especially, when the content of the lower alcohol is 1.0 to 25.0% by weight, based upon the total amount of the composition, when the lower alcohol is ethanol or isopropanol, or when the silicone oil is cyclic dimethylpolysiloxane, the desired advantageous effects can be obtained.

DESCRIPTION OF THE PREFERRED EMBODIMENTS

The mode of carrying out the present invention will now be explained.

The gelatinous compositions of the present invention are those containing one or more silicone oils.

The silicone oils formulated in the gelatinous composition of the present invention are not specifically limited and include, for example, low to high viscosities diorganopolysiloxanes such as dimethyl polysiloxane, methylphenyl polysiloxane, dimethylsiloxane methylphenylsiloxane copolymer; cyclic polysiloxane such as octamethyl cyclotetrasiloxane, decamethyl cyclopentasiloxane, tetramethyl tetraphenyl cyclotetrasiloxane; cyclic siloxane solutions of gum-like dimethyl polysiloxanes, gum-like dimethylsiloxane methylphenyl siloxane copolymer, gum-like dimethylpolysiloxane, etc., having high degree of polymerization; cyclic siloxane of trimethylsiloxy silicic acid, trimethylsiloxy silicic acid, etc. and further include, for example, diorgano polysiloxane having a $C_6$–$C_{50}$ alkyl group, amino-modified silicone, alkyl-modified silicone, fluorine-modified silicone etc.

Among these, cyclic polysiloxanes, especially cyclic dimethylpolysiloxanes such as octamethyl cyclotetrasiloxane, decamethyl cyclopentasiloxane, etc. are preferable to provide the gelatinous composition having an extremely excellent stability with the elapse of time.

Although the content of the silicone oil in the gelatinous composition of the present invention is not specifically limited, the preferable content is 80% by weight or less. When the content is more than 80% by weight, the stability of the gel with the elapse of time tends to become poor.

The gelatinous composition of the present invention further contains one or more polyether-modified silicone having the above-mentioned formula (I). This polyether-modified silicone (I) is an organopolysiloxane having at least one polyoxyalkylene group in one molecule thereof.

In the formula (I), A independently represents a methyl group, phenyl group or polyoxyalkylene group having the formula (II).

(II)

In the formula (II), a hydrogen atom, an acyl group or an alkyl group having 1 to 4 carbon atoms. Examples of the acyl group of R' are a formyl group, acetyl group, propionyl group, butyryl group, acryloyl group, benzoyl group, toluoyl group. Examples of the alkyl group having 1 to 4 carbon atoms are a methyl group, ethyl group, i-propyl group, n-propyl group, t-butyl group, n-butyl group.

Furthermore, a and b are independently an integer of 0–50, provided that both a and b are not zero. When both a and b are zero, unpreferably, the polyether-modified silicone does not exhibit the sufficient viscosity increasing or thickening effect. When a and/or b are more than 50, the resultant gelatinous composition exhibits the unpreferable stickiness feeling at the time of use.

In the formula (I), m is an integer of 1 to less than 50, preferably 5 to 48 and n is an integer of 1 to 40. When m is zero and/or n is zero, unpreferably, the resultant polyether-modified silicone does not exhibit the sufficient thickening effect. On the other hand, when m is not less than 50 and/or n is more than 40, the resultant gelatinous composition unpreferably provides the stickiness feeling at the time of use.

Example of the methyl group, a part of which is substituted with a fluorine atom are a fluoromethyl group, difluoromethyl group, etc and examples of the phenyl group, a part of which is substituted with a fluorine atom is a fluorophenyl group, etc.

Although the content of the polyoxyalkylene group (II) in the polyether-modified silicone (I) is not specifically limited, the preferable content is 40 to 55% by weight and the especially preferable content is 40 to 50% by weight. When the content of the polyoxyalkylene group is less than 40% by weight, the thickening effect of the resultant polyether-modified silicone tends to be unpreferably remarkably decreased. Contrary to this, when the content is more than 70% by weight, the compatibility with the silicone oil tend to be unpreferably decreased and also the thickening effect tends to be unpreferably decreased.

Further, there are no specific limitations to the molecular weight and the viscosity at 25° C. of the polyether-modified silicone (I) formulated in the gelatinous composition of the present invention, but the preferable weight-average molecular weight is 20,000 to 80,000.

In the present gelatinous composition, although there are no specific limitation to the content of the polyether-modified silicone (I), the content is preferably 2 to 50% by weight, more preferably 5 to 40% by weight, based upon the total amount of the composition. When the content of the polyether-modified silicone is less than 2% by weight, based upon the total weight of the composition, the formation of the stable gelatinous composition tends to be unpreferably difficult, whereas when the content is more than 50% by weight, the resultant gelatinous composition tends to unpreferably possess the stickiness feeling at the time of use.

The present gelatinous composition further contains water. Although the content of the water in the present gelatinous composition is not specifically limited, the content is preferably 0.2 to 80% by weight, more preferably, 10 to 40% by weight, based upon the total amount of the composition. When the content of water is less than 0.2% by weight of the total weight of the composition, the sufficiently stable gelatinous composition tends to be unpreferably difficult. Contrary to this, when the content of the water is more than 80% by weight, the resultant gelatinous composition tends to be unpreferably easily separated from the water, and therefore, the formation of the sufficiently stable gelatinous composition tends to be unpreferably difficult.

The present gelatinous composition further contain one or more lower alcohols.

Although the kinds of the lower alcohols usable in the present gelatinous composition are not specifically limited, the use of those having 1 to 4 carbon atoms, such as methanol, ethanol, i-propanol, n-propanol, t-butanol, sec-butanol, etc. is preferable. These lower alcohols have the effect to remarkably improve the stability of the gelatinous composition with the elapse of time. Among these lower alcohols, the use of ethanol and i-propanol, especially ethanol, is preferable.

The content of the lower alcohols in the present gelatinous composition is preferably 1 to 25% by weight, more preferably 5 to 10% by weight, based upon the total amount of the composition. When the content of the lower alcohols based upon the total weight of the composition is less than 1% by weight or more than 25% by weight, the stability of the resultant gelatinous composition with the elapse of time is unpreferably decreased.

In the gelatinous composition of the present invention, in addition to the above-mentioned essential ingredients, it is possible to formulate therein components conventionally used in the gelatinous compositions such as a humectant, surfactant, ultraviolet (U.V) absorber, antioxidant, preservative, antifungal agent, drug, extender pigment, coloring pigment, fragrance etc, so long as the intended effects of the present invention are not impaired.

The gelatinous composition of the present invention can be advantageously used in the fields of drugs, quasi-drugs or cosmetics, especial external use thereof. The present gelatinous composition may be used as, for example, a gelatinous foundation, sun screen gel, moisture gel, gelatinous cosmetic base, cleaning or make-up removal gel, hair gel, antiperspirant gel, etc.

EXAMPLES

The present invention will now be further illustrated by, but is by no means limited to, the following Examples. The formulation amounts in these Examples and Comparative Examples are all % by weight, based upon the total weight of the system to be formulated, unless otherwise noted the compositions in the following Examples and Comparative Examples were evaluated with respect to the organoleptic evaluation and the determination of stability with the elapse of time as follows.

Organoleptic Evaluation

The spreadability, refreshness, familiarity to skin, non-stickiness and cosmetic persistency were organoleptically evaluated by a cosmetically expert panel consisting of 10 women member at the ages of 20 to 40 under the following criteria:

++: Good judgement by 8 members/10 members
+: Good judgement by 6–7 members/10 members
±: Good judgement by 4–5 members/10 members
−: Good judgement by 3 or less members/10 members The cosmetic persistency was evaluated, the panel members walked for 2 hours after applying the sample to the face and the degree of the disorder of the sample cosmetic was visually self-observed. The "good of cosmetic persistency" means such a condition that no substantial or slight disorder of the cosmetic was visually self-observed.

Determination of Stability with Time

Each gelatinous composition obtained in the following Examples and Comparative Examples was filled in 4 glass bottles and was allowed to stand in the constant temperature vessel at a temperature of 50° C., 40° C., 20° C. or 0° C. for one month and the results, i.e., separation and the generation of color stripe, coagulation and sedimentation, were visually observed and evaluated as follows:

+: No change compared with the sample before setting in the constant temperature bath.

—: Separation etc. were found in a part of the four glass bottles.

Effect of Polyoxyalkylene Content on Viscosity of Composition

To evaluate the thickening effect of the polyether-modified silicone having the various polyoxyalkylene group content, the viscosity of the gelatinous composition was determined as follows.

A gelatinous composition was obtained by mixing 40% by weight of a polyether-modified silicone having a polyoxyalkylene group content shown in Table 1, 40% by weight of decamethyl pentasiloxane, and 20% by weight of water in a disper. The viscosity of the resultant gelatinous composition was determined using a B-type viscometer at 30° C. under the following conditions.

For viscosity of 1,000–10,000 mPa.s:
   Rotor No. 3, 12 rpm
For viscosity of 10,000–50,000 mPa.s:
   Rotor No. 4, 12 rpm
For viscosity of more than 50,000 mPa.s:
   Rotor No. 6, 10 rpm The results are shown in Table 1.

TABLE 1

| Run No. | Content of Polyoxyalkylene (wt %) | Viscosity (mPa · s) |
|---|---|---|
| 1 | 10 | 3,000 |
| 2 | 16 | less than 1,000 |
| 3 | 23 | 7,000 |
| 4 | 25 | 7,000 |
| 5 | 38 | 5,000 |
| 6 | 40% | more than 50,000 |
| 7 | 50% | 32,000 |
| 8 | 55% | 14,000 |
| 9 | 58% | 2,000 |
| 10 | 70% | 5,000 |

Note:
Although this sample composition does not contain a lower alcohol, the lower alcohol is intended to formulate in the gelatinous composition for the purposes of providing good stability with time and dewiness at the time of use and does not affects the thickening effect.

Examples 1–2 and Comparative Examples 1–6

Foundation

The foundations having the following formulations were prepared according to the preparation method mentioned below and the organoleptic evaluation test and the evaluation of stability thereof with the elapse of time were carried out. The results are shown in Table 2, in which the kinds of (8) polyether-modified silicone, the states and hardness of the resultant foundation are shown. The polyether-modified silicones A–E shown in Table 2 are the polyether-modified silicones having the formula (III) below and m, n, a, and b in the formula (III), the content of the polyoxyalkylene group and the molecular weight (calculation value) are shown in Table 3.

Decamethylpentacyclosiloxane in Comparative Example 1, microcrystalline wax (F) in Comparative Example 5, and dextrin fatty acid ester (G) in Comparative Example 6 were used respectively, instead of the polyether-modified silicone.

| Component | Amount (wt %) |
|---|---|
| (1) Silicone-treated talc | 10.0 |
| (2) Silicone-treated cericite | 3.0 |
| (3) Silicone-treated mica | 3.0 |
| (4) Silicone-treated titanium dioxide | 6.0 |
| (5) Silicone-treated coloring material | 3.0 |
| (6) Organopolysiloxane spherical powder (Torayfil E-506C available from Toray Dowcorning) | 8.0 |
| (7) Decamethyl pentercyclosiloxane | 44.0 |
| (8) Polyether-modified silicone having the formula (III) | 10.0 |
| (9) Diglyceryl diisostearate | 1.0 |
| (10) Ethanol | 6.0 |
| (11) Purified water | 6.0 |

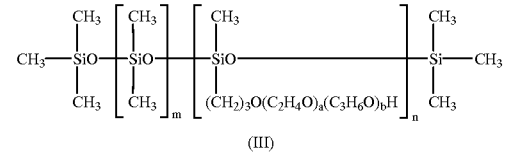

(III)

Preparation Method

After the component (6) was dispersed in the component (7), the powders of (1)–(5) were dispersed therein. Then, (8) and (9) were dissolved therein to form an oil phase part. On the other hand, (10) and (11) were mixed to prepare an aqueous phase part, which was added to the oil phase part with stirring. After deaeration, the resultant gelatinous composition was filled in a container to obtain the desired foundation.

TABLE 2

| | Example | | Comparative Example | | | | | |
|---|---|---|---|---|---|---|---|---|
| | 1 | 2 | 1 | 2 | 3 | 4 | 5 | 6 |
| Kind of (8) | A | B | None | C | D | E | F | G |
| Organoleptic test | | | | | | | | |
| Spreadability | ++ | ++ | − | ++ | ++ | ++ | − | − |
| Refreshness | ++ | ++ | − | + | + | + | ± | − |
| Familiarity to skin | ++ | ++ | − | + | + | + | ± | − |
| Non-stickiness | ++ | + | ± | ++ | ++ | ± | − | − |
| Cosmetic persistency | ++ | ++ | − | ++ | ++ | ++ | ± | ± |
| State | gelatinous | gelatinous | liquid | liquid | liquid | gelatinous | solid | solid |

TABLE 2-continued

|  | Example | | Comparative Example | | | | | |
| --- | --- | --- | --- | --- | --- | --- | --- | --- |
|  | 1 | 2 | 1 | 2 | 3 | 4 | 5 | 6 |
| Stability with time | + | + | − | − | − | + | − | − |
| Hardness[*1] at 30° C. | 24 | 26 | Non[*2] | Non[*2] | Non[*2] | 30 | Non[*2] | Non[*2] |

[*1]The determination of the hardness was carried out using a cardtension meter under the conditions of 200 g load and 8φ pressure sensitive axis
[*2]Non-measurable

TABLE 3

| Polyether-modified silicone | A | B | C | D | E |
| --- | --- | --- | --- | --- | --- |
| m | 25 | 45 | 25 | 25 | 400 |
| n | 3 | 8 | 3 | 3 | 10 |
| a | 10 | 3 | 5 | 28 | 24 |
| b | 0 | 5 | 0 | 0 | 24 |
| Content (wt %) of polyoxyalkylene group | 41 | 49 | 28 | 64 | 45 |
| Molecular weight (calc.) | 3700 | 7800 | 3000 | 6100 | 55000 |

From the results shown in Tables 2 and 3, when the content of the polyoxyalkylene group in the polyether-modified silicone (I) is 40–50% by weight, the gelatinous foundation exhibit excellent stability with the elapse of time as well as no stickiness in the feeling at the time of use, light spreadability and refreshing feeling when applied to the skin, good familiarity to the skin and good cosmetic persistency.

Formulation Examples of other gelatinous compositions according to the present invention will now be illustrated.

Example 3
Sunscreen Gel

| Component | Amount (wt %) |
| --- | --- |
| (1) Decamethylcyclopentasiloxane | 48.0 |
| (2) Dimethylpolysiloxane (6CS) | 2.0 |
| (3) Methylphenyl polysiloxane (20CS) | 5.0 |
| (4) Ethanol | 8.0 |
| (5) Polyether-modified silicone having the formula (IV) | 10.0 |
| (6) Ion exchanged water | 20.0 |
| (7) 2-Ethylhexyl p-methoxycinnamate | 5.0 |
| (8) Paraben | q.s. |
| (9) Antioxidant | q.s. |
| (10) Fragrance | q.s. |

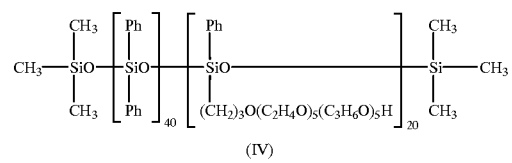

(IV)

wherein Ph represents a phenyl group

Preparation Method

After dissolving (1)–(3) and (7)–(10) with mixing at room temperature, (5) was added, while stirring with a homomixer to be thoroughly mixed. Thereafter, while containing to mix with the homomixer, (4) and (6) were added to came the gelatin, whereby the desired sunscreen gel was obtained.

The resultant sunscreen gel had no stickiness at the time of use, excellent stability with the elapse of time, and light spreadability on the skin and refreshing feeling when applied.

Example 4
Hair Gel

| Component | Amount (wt %) |
| --- | --- |
| (1) Decamethylcyclopentasiloxane | 44.0 |
| (2) Dimethylpolysiloxane (6CS) | 2.0 |
| (3) i-Propanol | 20.0 |
| (4) Polyether-modified silicone having the formula (V) | 10.0 |
| (5) Ion-exchanged water | 20.0 |
| (6) Polyvinylpyrrolidone | 2.0 |
| (7) Glycerol | q.s. |
| (8) Paraben | q.s. |
| (9) Antioxidant | q.s. |
| (10) Fragrant | q.s. |

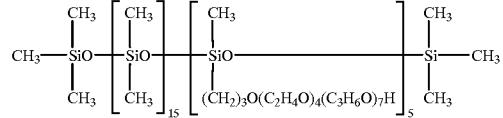

(V)

Preparation Method

After mixing (1), (2) and (6)–(10) and having at 80° C., the mixture was cooled to a room temperature followed by adding (4) with stirring. While stirring with a homomixer, (3) and (5) were added thereto to form a gel. Thus, the desired hair gel was obtained.

The resultant hair gel exhibited extremely excellent stability with the elapse of time, no stickiness during the use thereof and light spreadability on the skin and refresh feelings at the time of use.

Example 5
Moisture Gel

| Component | Amount (wt %) |
| --- | --- |
| (1) Decamethylcyclopentasiloxane | 47.0 |
| (2) Dimethylpolysiloxane (6CS) | 2.0 |
| (3) i-Propyl alcohol | 1.0 |
| (4) Polyether-modified silicone having the formula (VI) | 10.0 |
| (5) Ion-exchanged water | 20.0 |
| (6) 1,3-Butylene glycol | 10.0 |
| (7) Polyethylene glycol 1500 | 8.0 |
| (8) Paraben | q.s. |
| (9) Antioxidant | q.s. |
| (10) Fragrant | q.s. |

-continued

| Component | Amount (wt %) |
|---|---|

H(OC$_3$H$_6$)$_{10}$(OC$_2$H$_4$)$_{10}$O(CH$_2$)$_3$—[Si(CH$_3$)$_2$O]—[Si(CH$_3$)$_2$O]$_{30}$—[Si(CH$_3$)(—(CH$_2$)$_3$O(C$_2$H$_4$O)$_{10}$(C$_3$H$_6$O)$_{10}$H)O]—

(VI)

The moisture gel was obtained in the same manner as in Example 4.

The resultant moisture gal exhibited extremely excellent stability with the elapse of time, no stickiness at the time of use, light spreadability on the skin and refresh feelings.

Example 6
Gelatinous Cosmetic Base

| Component | Amount (wt %) |
|---|---|
| (1) Ion-exchanged water | Balance |
| (2) 1,3-Butylene glycol | 3.0 |
| (3) Methyl paraben | 0.15 |
| (4) Polyether-modified silicone having the formula (VII) | 8.0 |
| (5) Decametylcyclopentasiloxane | 45.0 |
| (6) Octylmethoxycinnamate | 5.0 |
| (7) Dimethylpolysiloxane | 10.0 |
| (8) Nylon powder | 6.0 |
| (9) Ethanol | 5.0 |

CH$_3$—[Si(CH$_3$)$_2$O]—[Si(CH$_3$)$_2$O]$_{30}$—[Si(CH$_3$)((CH$_2$)$_3$O(C$_3$H$_6$O)$_{10}$H)O]$_5$—Si(CH$_3$)$_3$ (VII)

Preparation Method (3)–(7) were mixed and dissolved at 40° C., where (8) was uniformly dispersed to prepare an oil phase. To this oil phase, (1), (2) and (9) were added, while sufficiently stirring, followed by uniformly mixing with a homomixer. The resultant composition was deaerated and filtered to obtain the gelatinous cosmetic base.

The resultant cosmetic base exhibited extremely excellent stability with the elapse of time, no stickiness in feeling and light spreadability on the skin and refreshing feeling at the time of use.

As explained above, according to the present invention, there is provided a gelatinous composition exhibiting, extremely excellent stability with the elapse of time, no stickiness in feeling and light spreadability or the skin and refreshing feeling at the time of use.

What is claimed is:

1. A gelatinous composition consisting essentially of:
   (i) at least one silicone oil,
   (ii) at least one polyether-modified silicone having the formula (I):

$$A-SiR_2O-[SiR_2O]_m-[SiRAO]_n-SiR_2-A \quad (I)$$

wherein A independently represents a group selected from the group consisting of a methyl group, phenyl group and polyoxyalkylene group having the formula (II)

$$-C_3H_6O(C_2H_4O)_a(C_3H_6O)_bR' \quad (II)$$

wherein R' is a group selected from the group consisting of a hydrogen atom, an acyl group and alkyl group having 1 to 4 carbon atoms, a and b are independently an integer of 0 to 50, provided that both a and b are not zero, R independently represents a methyl group or phenyl group, m is an integer of 1 to less than 50 and n is an integer of 1 to 40, provided that a part of the methyl group, phenyl group and polyoxyalkylene group any be substituted with a fluorine atom, and 41 to 55% by weight of the polyoxyalkylene group of formula (II) is present in one molecule, (iii) water, (iv) at least one lower alcohol and (v) one or move optional components selected from the group consisting of a humectant, a surfactant, an ultraviolet absorber, an antioxidant, a preservative, an antifungal agent, a drug, an extender pigment, a coloring pigment and a fragrance ingredient.

2. A gelatinous composition as claimed in claim 1, wherein the content of the silicone oil is 80% by weight or less, based upon the total amount of the composition.

3. A gelatinous composition as claimed in claim 1, wherein the content of the polyether-modified silicone (I) is 2 to 50% by weight, based upon the total amount of the composition.

4. A gelatinous composition as claimed in claim 1, wherein the content of water is 0.2 to 80% by weight, based upon the total amount of the composition.

5. A gelatinous composition as claimed in claim 1, wherein the content of the lower alcohol is 1.0 to 25.0% by weight, based upon the total amount of the composition.

6. A gelatinous composition as claimed in claim 1, wherein the lower alcohol is ethanol or isopropanol.

7. A gelatinous composition as claimed in claim 1, wherein the silicone oil is cyclic dimethylpolysiloxane.

8. A gelatinous composition as claimed in claim 1, wherein the content of the polyoxyalkylene group in the polyether-modified silicone is 41 to 50% by weight.

9. A cosmetic composition consisting of the composition of claim 1.

* * * * *